United States Patent [19]

DeMarinis et al.

[11] Patent Number: 4,507,320

[45] Date of Patent: Mar. 26, 1985

[54] DOPAMINERGIC AGONIST N,N-DI-N-PROPYL-4-HYDROXY-3-METHANESULFONAMIDOPHENETHYLAMINE

[75] Inventors: Robert M. DeMarinis, Ardmore; J. Paul Hieble, Philadelphia, both of Pa.; Carl Kaiser, Haddon Heights, N.J.; James W. Wilson, Wayne, Pa.

[73] Assignee: Smithkline Beckman Corporation, Philadelphia, Pa.

[21] Appl. No.: 559,151

[22] Filed: Dec. 7, 1983

[51] Int. Cl.$^3$ .................. C07C 143/75; A61K 31/18
[52] U.S. Cl. .................. 514/605; 260/456 A; 560/109; 560/251; 564/99
[58] Field of Search .......... 564/99; 260/456 A; 560/109, 251; 424/303, 308, 311, 321

[56] References Cited

U.S. PATENT DOCUMENTS

| | | | |
|---|---|---|---|
| 3,341,584 | 9/1967 | Larsen et al. | 564/99 X |
| 3,574,741 | 4/1971 | Gould et al. | 564/99 X |
| 3,660,487 | 5/1972 | Larsen et al. | 564/99 X |
| 3,701,808 | 10/1972 | Hartley et al. | 564/99 |
| 3,758,692 | 9/1973 | Larsen et al. | 424/321 |
| 3,801,631 | 4/1974 | Comer et al. | 564/99 X |
| 4,219,568 | 8/1980 | Goldberg et al. | 424/330 |
| 4,404,224 | 9/1983 | Asato | 564/99 X |

OTHER PUBLICATIONS

Uloth et al., J. Med. Chem., vol. 99, pp. 88–96, (1966).
Larsen et al., CA 71: 30232k, (1969).
H. Sheppard et al., "Cyclic Nucleotides in Disease", University Park Press, 1974.

*Primary Examiner*—Thomas A. Waltz
*Attorney, Agent, or Firm*—William H. Edgerton; Richard D. Foggio; Alan D. Lourie

[57] ABSTRACT

N,N-Di-n-propyl-4-hydroxy-3-methanesulfonamidophenethylamine is a potent, selective presynaptic dopaminergic agonist. The compound is prepared by N-sulfonylation of an optionally O-protected derivative of 3-amino-4-hydroxy-N,N-di-n-propylphenethylamine, followed by removal of the protecting group.

12 Claims, No Drawings

DOPAMINERGIC AGONIST N,N-DI-N-PROPYL-4-HYDROXY-3-METHANESULFONAMIDOPHENETHYLAMINE

This invention relates to a new chemical compound, N,N-di-n-propyl-4-hydroxy-3-methanesulfonamidophenethylamine, which is a potent and selective presynaptic dopaminergic ($DA_2$) agonist. Also included in this invention are new pharmaceutical compositions and methods for treating cardiovascular disorders by means of a peripheral $DA_2$ agonist mechanism of action, i.e. by stimulation of the receptors located on the presynaptic post-ganglionic sympathetic nerves.

BACKGROUND OF THE INVENTION

U.S. Pat. No. 3,574,741 discloses a large group of sulfonamidophenylalkylamines which are alleged therein to have activity as highly active sympathomimetic agents which have pressor activity useful for constricting blood vessels, especially in the eye or in the nasal passage.

U.S. Pat. No. 4,219,568 discloses that a number of dopamine congeners increase renal blood flow without affecting cardiac contractility.

H. Sheppard et al., "Cyclic Nucleotides in Disease" University Park Press, 1974, at page 125, discloses that the 3-methylsulfonamido analogue of dopamine was weaker than was dopamine itself as an agonist for adenylate cyclase in the caudate nucleus.

The species of the present invention is not disclosed in the cited art and the pharmacodynamic activity of this compound is unexpected.

DESCRIPTION OF THE INVENTION

The basic compound of this invention has the following structural formula:

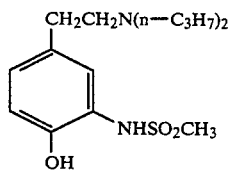

Also included are pharmaceutically acceptable salts of this compound. Such salts include those formed by reacting the base of formula I with a nontoxic acid, for example, hydrochloric, hydrobromic, sulfuric, phosphoric, sulfamic, maleic, methanesulfonic, ethanedisulfonic or nitric acid. These salts are prepared by methods known to the art, most conveniently by reacting the base with an excess of the chosen acid in an organic solvent. Other salts, which are less used, are the phenolic metal salts such as the sodium or potassium salts. Prodrug derivatives, for example, the O-lower alkanoyl or aralkanoyl containing esters, are also part of this invention.

N,N-Di-n-propyl-4-hydroxy-3-methanesulfonamidophenethylamine is prepared conveniently by the following reactions:

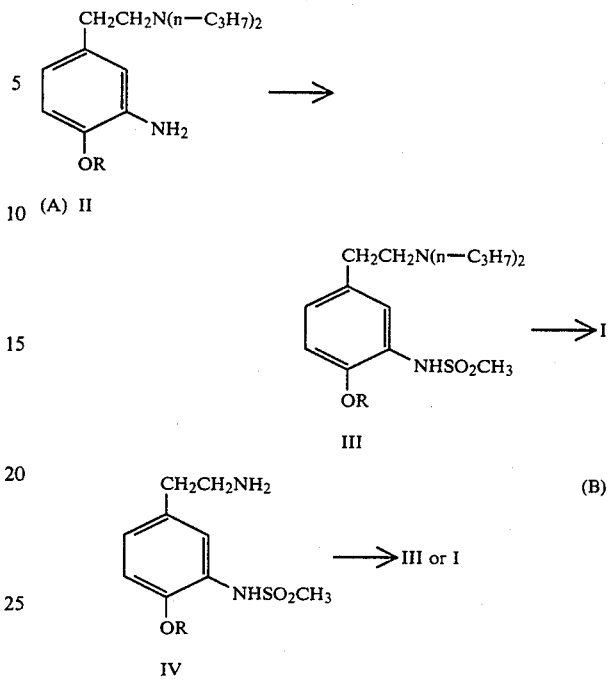

in which R is a hydroxy protecting group as known to the art, such as benzyl, benzhydryl or trityl which are easily removed by catalytic hydrogenation or metal hydride reduction.

The preferred route involves N-sulfonylation of the primary amine (II) by reaction with methanesulfonyl chloride or bromide in the presence of an organic base, such as pyridine or dimethylaniline, either in excess or in an organic solvent, to give the O-protected form of the end product. The protecting R group is, then, removed by a chemical reaction which will not split the methanesulfonamido group, such as by catalytic hydrogenation over a noble metal catalyst, for example palladium-on-charcoal, in an organic solvent such as methanol, ethyl acetate, ethereal hydrogen chloride or mixtures thereof. The end product is isolated by methods known to the chemical art.

The alternative route comprises reaction of the O-protected phenethylamine intermediate (IV) with a N-alkylating agent, for example propionaldehyde in a reducing medium. The O-protecting group is, then, removed as described above. The starting materials are prepared as described in U.S. Pat. No. 3,574,741.

An alternative method of synthesis is to remove an α-hydroxy group from the α-hydroxy congener of III or IV either directly by hydrogenation or through the α-chloro intermediate as known to the art.

The unexpected biological spectrum of N,N-di-n-propyl-4-hydroxy-3-methanesulfonamidophenethylamine is demonstrated using a protocol to establish the desired $DA_2$ agonist activity. The procedure measures the ability of the test compound to inhibit the constrictor response of isolated perfused rabbit ear artery caused by field stimulation of its adrenergic nerve terminals. Activity in this test is, then, compared with undesired $alpha_1$-agonist activity which is determined in the superfused rabbit ear artery segment. Both protocols are described in J. P. Hieble, et al., Arch. Pharmacol. 309 218(1979).

In order to quantitate the DA₂ agonist activity of compounds B and C of Table 1 below, whose alpha₁-agonist effects prevented measurement of the effector response in the rabbit ear artery, a modification of the above test was used, in which the artery was prelabelled with ³H-norepinephrine (NE) and stimulation-evoked transmitter release was measured directly by counting the overflow of radioactivity. Compound A was also examined in this manner to compare the two methods of measuring DA₂ activity. This protocol is described in R. M. DeMarinis et al., J. Med. Chem. 26, 1215(1983).

TABLE 1

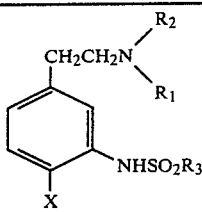

| COMPOUND** | $R_1$ | $R_2$ | $R_3$ | X | $EC_{50}$-$DA_2$(nM) (Effector Response) | $EC_{50}$-$DA_2$(nM) (³H-NE release) | $EC_{50}$-$\alpha_1$(nM) |
|---|---|---|---|---|---|---|---|
| A | n-C₃H₇ | n-C₃H₇ | CH₃ | OH | 2 | 10 | 760 |
| B | H | H | CH₃ | OH | >300* | 3000 | 355 |
| C | H | CH₃ | CH₃ | OH | >30* | 300 | 25 |
| D | H | i-C₃H₇ | CH₃ | OH | >1000 | NT | 2000 |
| E | n-C₃H₇ | n-C₃H₇ | CF₃ | OH | >1000 | NT | NT |
| F | n-C₃H₇ | n-C₃H₇ | CH₃ | H | 400 | NT | NT |
| G | H | H | CH₃ | H | >1000 | NT | NT |

*Higher concentrations could not be tested due to vasoconstriction.
**The compounds were tested in acid addition salt form.
NT = not tested.

The active species of this invention, Compound A of Table 1, has potent DA₂-agonist activity (EC₅₀ of 2 nM against effector response and 10 nM against norepinephrine release) with weak alpha₁-agonist activity (EC₅₀ of 760 nM) which demonstrates high selectivity for the desired peripheral DA₂ receptor sites. No alpha₁-mediated vasoconstriction was observed during these tests.

The primary amine, Compound B, is described, in column 3 of U.S. Pat. No. 3,574,741, to be the preferred compound of the invention described therein. This compound had only very weak DA₂ activity (EC₅₀=3000 nM versus NE release). Note also that, at 300 nM in the effector response test, vasoconstriction was observed which confirms the fact, as stated in the reference patent, that the primary amine has significant sympathomimetic or pressor activity.

Compound C is a secondary amine which is specifically disclosed in the U.S. Pat. No. 3,547,741 as Example 7 in Table II, column 12. The compound also demonstrates vasoconstriction as a result of alpha₁-agonist activity (EC₅₀=25 nM) and weaker DA₂ activity (EC₅₀=300 nM versus NE release).

Finally, Compounds D, E, F and G of Table 1 above demonstrate the specific structural configuration necessary for potent, selective DA₂-agonist activity.

Compound A of Table 1 was found to have no alpha₂-agonist activity in a standard protocol for this indication which involves the use of isolated guinea pig atrial tissue. Compounds B and C (of the U.S. Pat. No. 3,547,741 demonstrate significant α₂-activity in this protocol.

The specific presynaptic dopamine agonist (DA₂) activity of N,N-di-n-propyl-4-hydroxy-3-methanesulfonamidophenethylamine, which is demonstrated above, attenuates the release of norepinephrine from certain peripheral presynaptic terminals, thereby, counteracting the effect of high sympathetic drive which is present in certain abnormal cardiovascular conditions such as angina or hypertension. The cardiovascular manifestation of a DA₂-agonist mechanism of action of the compound of this invention is exactly opposite of that expected from the sympathomimetic activity which is described in U.S. Pat. No. 3,547,741 for its generic group of chemical compounds. Note that the latter activity is described to be manifested as pressor or vasoconstricting effects which would be strongly contraindicated for patients with angina or hypertension.

Thusly, the compound of formula I, its nontoxic salts and its prodrug forms are useful for treating animal and human subjects in need of a specific DA₂-agonist activity by administering to said subjects internally, preferably orally or parenterally, an effective therefor but nontoxic quantity of the base compound. Transdermal or rectal administration are alternatives. Specific clinical conditions whose treatment is the object of this invention include various abnormal cardiovascular conditions as described above but, specifically, angina and hypertension.

The term "nontoxic", as used herein, is meant to exclude any quantity of active ingredient which might induce limiting sympathomimetic effects, especially pressor or vasoconstrictor activity, as well as other overt toxic effects.

Preferably, an effective quantity of active base is selected from the dosage unit range of 1–100 mg, advantageously from about 10 mg to about 50 mg. Such quantity is administered to the subject from 1–4 times a day. Oral administration is preferred.

The pharmaceutical compositions of this invention for producing DA₂-adrenoceptor stimulation, which is manifested as anti-hypertensive and anti-anginal activity, comprise a pharmaceutical dosage unit carrier and, dispersed therein as the active ingredient, the compound of formula I, a salt or prodrug thereof. The active ingredient will be present in the compositions in an effective amount to produce DA₂ stimulation as well as the resulting cardiovascular activity but not to have limiting side effects as discussed above.

Preferably, the unit dosage compositions contain an effective quantity of the active ingredient of formula I, which is selected from the range of about 1 mg to about 100 mg, advantageously from about 10 mg to about 50 mg, of base equivalent per dosage unit.

The pharmaceutical carrier in which the active ingredient is dispersed is, for example, a solid or a liquid as known to the art. Exemplary of solid carriers are lactose, magnesium stearate, terra alba, sucrose, talc, stearic acid, gelatin, agar, pectin or acacia. The amount of solid carrier will vary widely, but preferably, will be from about 25 mg to about 1 gm. Exemplary of liquid carriers are syrup, peanut oil, olive oil, sesame oil, propylene glycol, polyethylene glycol and water. The carrier or diluent may include a time delay material known to the art such as, for example, a cellulose ether or ester derivative or a glycerol fatty acid ester, alone or admixed with waxes or other modifying agents.

A wide variety of pharmaceutical forms can be employed. For example, the preparation may take the form of tablets, capsules, powders, troches, lozenges, syrups, transdermal patches, suppositories, emulsions, sterile injectable liquids, liquid suspensions or liquid solutions, each calibrated for dosage unit quantities of the active ingredient.

The pharmaceutical compositions are prepared by conventional techniques involving procedures such as mixing, granulating and compressing or dissolving the ingredients as appropriate to the desired preparation.

In addition, for treating abnormal cardiovascular conditions, the compound of formula I may be combined with clinically useful quantities of one or more other cardiovascular agents, such as a diuretic agent, for example hydrochlorothiazide, triamterene or furosemide, a calcium channel blocker, for example nifedipine or verapamil, a $\beta$-adrenergic blocker, for example propanolol, a ACE inhibitor such captopril or a cardiotonic agent such as amrinone or milrinone.

The following examples are intended to teach specific aspects of this invention as an illustration of the preparation of the active ingredients described above and their use. All temperatures are Centigrade.

EXAMPLE 1

A mixture of 91.8 g (0.552 mol) of 4-methoxyphenylacetic acid and 75 ml (124.5 g, 1.05 mol) of thionyl chloride in 500 ml of toluene and 2 ml of dimethylformamide was stirred overnight. The reaction mixture was stripped to dryness with additional toluene. Di-n-propylamine (150 ml) in methylene chloride was added and the mixture was refluxed overnight. After stripping off methylene chloride and most of the amine, the mixture was partitioned between ether and water. The ether phase was washed with 10% hydrochloride acid, 10% sodium hydroxide solution and water. The organic extract was dried and evaporated to give 127.2 g (92%) of an amber colored oil, N,N-di-n-propyl-4-methoxyphenylacetamide.

To a solution of 750 ml (0.735 mol) of 0.98M boron hydride in tetrahydrofuran was added a solution of 127.2 g (0.51 mol) of the crude acetamide in tetrahydrofuran. A gel formed which was broken up with a mechanical stirrer. The mixture was refluxed 4 hours, treated with methanol, stirred several days and stripped to a yellow oil. After treating with dilute hydrochloride acid on a steam bath for 2 hours, the mixture was cooled and extracted with ether. The aqueous solution was basified with 40% sodium hydroxide solution and extracted with ether. Drying and evaporating the ether gave 101 g of a yellow oil which was distilled at 113°–116°/0.5 mm to give 90.3 g (75.3%) of colorless oil, N,N-di-n-propyl-4-methoxyphenethylamine.

Anal. Calcd. for $C_{15}H_{25}NO$: C, 76.55; H, 10.71; N, 5.95; Found: C, 76.70; H, 10.66; N, 5.94.

A mixture of 90.3 g of the methoxy compound (0.384 mol) and 400 ml of freshly distilled hydrobromic acid (48%) was refluxed 3 hours and stripped to a crystalline residue. Recrystallization from methanol and ether gave 102 g (88%) of N,N-(di-n-propyl)-4-hydroxyphenethylamine, as a white crystalline solid, m.p. 158°–160°.

To a solution of 48.1 g (0.160 mol) of the hydroxy compound in 250 ml of acetic acid was added 13.85 ml (19.5 g, 0.217 mol) of 70% nitric acid. The mixture was stirred overnight, then diluted with water, neutralized with ammonium hydroxide and extracted with ethyl acetate. The extract was dried and evaporated to give a 49.3 g residue. Chromatographic purification (dry column) of the residue yielded 10.6 g of starting material and 23.5 g (62%) of the nitro product, m.p. 263°.

A mixture of 23.5 g (0.0883 mol) of the nitro product, 40 g (0.29 mol) of potassium carbonate and 10.5 ml (15.1 g, 0.0883 mol) of benzyl bromide in 500 ml of acetone was refluxed for 2 hours. After filtration and evaporation, the residue was heated in ethyl acetate, cooled and some quaternary salt filtered off. The filtrate was evaporated to give 30.2 g of crude 4-benzyloxy-N,N-di-n-propyl-3-nitrophenethylamine which was chromatographed on a dry column with 1:1 ether/petroleum ether which afforded 23.1 g (73.5%) of purified product as an orange oil.

To a solution of 23.1 g (0.0648 mol) of benzyloxy compound in methanol was added 0.35 g of platinum oxide and a small amount of ethereal hydrogen chloride. The mixture was hydrogenated on a Parr shaker, filtered and the filtrate stripped of solvent. Addition of isopropanol and ethereal hydrogen chloride slowly precipitated the hydrochloride salt of 3-amino-4-benzyloxy-N,N-di-n-propylphenethylamine, 24.8 g, light tan crystalline solid, m.p. 100°–105°. Recrystallization from isopropanol and ether gave crystals, m.p. 107°–110°.

Anal. Calcd. for $C_{21}H_{30}N_2O.2HCl.2H_2O$: C, 57.93; H, 8.33; N, 6.43. Found: C, 57.75; H, 8.04; N, 6.60.

To a mixture of 3.0 g (0.0093 mol) of the amine and 100 ml of dry pyridine was added 3.16 g (2.14 ml, 0.028 mol) of methanesulfonyl chloride. The mixture was heated on a steam bath for 4 hrs., then, stirred overnight at room temperature. The mixture was diluted with water, basified to pH 10 with 10% sodium hydroxide solution and extracted twice with ethyl acetate. The dried extract was washed twice with water, treated with carbon black and, with the addition of toluene, evaporated to dryness to yield 3.8 g (100%) of N-2-benzyloxy-5-(N'N'-dipropylaminoethylphenyl)-methanesulfonamide, used in the following reduction. A sample, treated with ether and pentane, formed a yellow-tan crystalline solid, m.p. 51.5°–53°.

Anal. Calcd. for $C_{22}H_{32}N_2O_3S$: C, 65.31; H, 7.97; N, 6.92. Found: C, 65.00; H, 8.17; N, 6.87.

A solution of 3.6 g (0.0087 mol) of the benzyl ether in methanol, ethyl acetate and ethereal hydrogen chloride was hydrogenated over 0.75 g of 10% palladium-on-charcoal on a Parr shaker. Uptake was slow. The mixture was filtered, evaporated and converted to the free base, N,N-di-n-propyl-4-hydroxy-3-methanesulfonamidophenethylamine. The base was treated with fumaric acid in ethyl acetate to give the fumarate salt of the product; 2.0 g (64%), m.p. 155°–157°.

Anal. Calcd. for $C_{34}H_{56}N_4O_{10}S_2 \cdot 0.5H_2O$: C, 54.16; H, 7.64; N, 7.43. Found: C, 54.28; H, 7.48; N, 7.31.

Equal 500 mg portions of the base in ethyl acetate are treated with excess hydrogen chloride and methanesulfonic acid, respectively, to give the hydrochloride and methanesulfonate salts.

EXAMPLE 2

| Ingredients | Amounts |
| --- | --- |
| N,N—Di-n-propyl-4-hydroxy-3-methane-sulfonamidophenethylamine hydrochloride (base equivalent) | 50 mg. |
| Calcium sulfate dihydrate | 200 mg. |
| Sucrose | 15 mg. |
| Starch | 10 mg. |
| Talc | 5 mg. |
| Stearic Acid | 3 mg. |

The calcium sulfate dihydrate, sucrose and active ingredients are thoroughly mixed and granulated with a 10% gelatin solution. The wet granules are screened, dried, then, mixed with the starch, talc and stearic acid, screened and compressed into a scored tablet.

One tablet is administered orally three times a day to a human patient in need of $DA_2$-stimulation.

What is claimed is:

1. A method for inducing $DA_2$-agonist activity in a subject in need thereof comprising administering internally to said subject a nontoxic, effective therefor quantity of N,N-di-n-propyl-4-hydroxy-3-methanesulfonamidophenethylamine, a prodrug derivative thereof or a pharmaceutically acceptable salt thereof.

2. The method of claim 1 in which the $DA_2$-agonistic activity is manifested by anti-anginal activity.

3. The method of claim 1 in which the $DA_2$-agonistic activity is manifested by anti-hypertensive activity.

4. The method of claim 1 in which the N,N-di-n-propyl-4-hydroxy-3-methanesulfonamidophenethylamine is in the form of the hydrochloride salt.

5. The method of claim 1 in which the effective quantity of N,N-di-n-propyl-4-hydroxy-3-methanesulfonamidophenethylamine is selected from the range of 1–100 mg of base equivalent and is administered orally from 1–4 times daily.

6. A pharmaceutical composition having $DA_2$-agonistic activity comprising a nontoxic, effective therefor quantity of N,N-di-n-propyl-4-hydroxy-3-methanesulfonamidophenethylamine, a prodrug derivative thereof or a pharmaceutically acceptable salt thereof combined with a pharmaceutical carrier.

7. The composition of claim 6 in which the quantity of N,N-di-n-propyl-4-hydroxy-3-methanesulfonamidophenethylamine base equivalent is selected from the range of 1–100 mg.

8. The composition of claim 7 in which the quantity is selected from the range of 10–50 mg. of base equivalent.

9. N,N-Di-n-propyl-4-hydroxy-3-methanesulfonamidophenethylamine, a prodrug derivative thereof or a pharmaceutically acceptable salt thereof.

10. The compound of claim 9 being the hydrochloride salt.

11. The compound of claim 9 being the base.

12. The compound of claim 9 being the methanesulfonate salt.

* * * * *